(12) United States Patent
Bui et al.

(10) Patent No.: US 9,272,039 B2
(45) Date of Patent: *Mar. 1, 2016

(54) STRUCTURED NON-AQUEOUS GEL-FORM CARRIER COMPOSITION

(75) Inventors: Hy Si Bui, Piscataway, NJ (US); Mohamed Kanji, Edison, NJ (US); Liana Esposito, Franklin Park, NJ (US)

(73) Assignee: L'ORÉAL (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/583,682

(22) PCT Filed: Mar. 10, 2011

(86) PCT No.: PCT/US2011/027877
§ 371 (c)(1),
(2), (4) Date: Sep. 10, 2012

(87) PCT Pub. No.: WO2011/112799
PCT Pub. Date: Sep. 15, 2011

(65) Prior Publication Data
US 2013/0004442 A1    Jan. 3, 2013

Related U.S. Application Data

(60) Provisional application No. 61/312,429, filed on Mar. 10, 2010, provisional application No. 61/312,552, filed on Mar. 10, 2010.

(51) Int. Cl.
| | |
|---|---|
| *A61Q 17/04* | (2006.01) |
| *A61Q 1/02* | (2006.01) |
| *A61Q 19/00* | (2006.01) |
| *A61Q 1/10* | (2006.01) |
| *A61K 8/90* | (2006.01) |
| *A61K 8/42* | (2006.01) |
| *A61K 47/18* | (2006.01) |
| *A61K 8/02* | (2006.01) |
| *A61K 8/34* | (2006.01) |
| *A61K 8/44* | (2006.01) |
| *A61K 8/81* | (2006.01) |
| *A61K 9/00* | (2006.01) |
| *A61K 9/06* | (2006.01) |
| *A61Q 1/06* | (2006.01) |

(52) U.S. Cl.
CPC .............. *A61K 47/18* (2013.01); *A61K 8/0229* (2013.01); *A61K 8/345* (2013.01); *A61K 8/442* (2013.01); *A61K 8/8111* (2013.01); *A61K 8/8164* (2013.01); *A61K 8/90* (2013.01); *A61K 9/0014* (2013.01); *A61K 9/06* (2013.01); *A61Q 1/06* (2013.01)

(58) Field of Classification Search
CPC ..... A61K 2800/31; A61K 8/442; A61Q 1/04; A61Q 19/00; A61Q 1/10; A61Q 5/06
USPC .................... 424/59, 63, 772.3, 401, 70.7, 64
See application file for complete search history.

(56) References Cited

U.S. PATENT DOCUMENTS

| | | | |
|---|---|---|---|
| 4,291,018 A | 9/1981 | Oeda et al. | |
| 5,424,070 A | 6/1995 | Kasat et al. | |
| 5,716,604 A | 2/1998 | Coe et al. | |
| 6,177,066 B1 | 1/2001 | Pataut et al. | |
| 7,244,419 B2 * | 7/2007 | Yamato et al. | 424/67 |
| 7,758,848 B2 | 7/2010 | Lu et al. | |
| 2002/0127192 A1 | 9/2002 | Murphy et al. | |
| 2002/0159961 A1 | 10/2002 | Yamato et al. | |
| 2004/0170586 A1 | 9/2004 | Ferrari et al. | |
| 2004/0229984 A1 | 11/2004 | Yamato et al. | |
| 2005/0220728 A1 | 10/2005 | Kanji et al. | |
| 2006/0078581 A1 | 4/2006 | Yamato | |
| 2006/0110345 A1 | 5/2006 | Lu et al. | |

(Continued)

FOREIGN PATENT DOCUMENTS

| | | |
|---|---|---|
| CN | 101087580 A | 12/2007 |
| EP | 1854451 A2 | 11/2007 |

(Continued)

OTHER PUBLICATIONS

International Search Report Application No. PCT/US2011/027877, dated Nov. 25, 2011.
International Search Report Application No. PCT/US2011/027866, dated Nov. 24, 2011.
International Search Report Application No. PCT/US2011/027873, dated Nov. 24, 2011.
International Search Report Application No. PCT/US2011/027880, dated Nov. 25, 2011.
International Search Report Application No. PCT/US2011/027887, dated Nov. 25, 2011.
Chinese Office Action for Application No. 201180023023.9 dated Oct. 29, 2013.
Chinese Office Action for Application No. 201180023037.0 dated Apr. 21, 2014.
Japanese Office Action for Application No. 2012-557242 dated May 7, 2014.

(Continued)

*Primary Examiner* — Frederick Krass
*Assistant Examiner* — Tracy Liu
(74) *Attorney, Agent, or Firm* — Lerner, David, Littenberg, Krumholz & Mentlik, LLP

(57) ABSTRACT

Disclosed are non-aqueous carrier compositions capable of forming a gel structure, having a low molecular mass N-acyl glutamic acid diamide having a straight-chain alkyl group, a low molecular mass N-acyl glutamic acid diamide having a branched-chain alkyl group, at least one gel-promoting solvent, and at least one high molecular mass block copolymer having at least one hard segment and at least one soft segment, and at least one solvent capable of solubilizing the at least one hard segment and/or the at least one soft segment of the block copolymer, at least one oil-soluble polar modified polymer; and at least one solvent capable of solubilizing the at least one oil-soluble polar modified polymer, and optionally at least one active ingredient, wherein the composition has a hardness value ranging from about 30 to about 300 gf, a melting point of about 50° C. or higher, and does not require use of wax as a structuring agent. Methods of making and using the compositions are also disclosed.

15 Claims, 1 Drawing Sheet

(56) References Cited

U.S. PATENT DOCUMENTS

| | | |
|---|---|---|
| 2006/0134037 A1 | 6/2006 | Cropper et al. |
| 2007/0128233 A1 | 6/2007 | Lu et al. |
| 2007/0243151 A1 | 10/2007 | Healy |
| 2007/0258923 A1 | 11/2007 | Bui et al. |
| 2008/0057011 A1 | 3/2008 | Ferrari |
| 2008/0102048 A1 | 5/2008 | McDermott |
| 2009/0280076 A1 | 11/2009 | Yoshida et al. |
| 2009/0280077 A1 | 11/2009 | Yoshida et al. |
| 2009/0317345 A1 | 12/2009 | Joshi et al. |
| 2010/0203097 A1 | 8/2010 | Tanaka |
| 2011/0150793 A1 | 6/2011 | Do et al. |
| 2012/0045493 A1 | 2/2012 | Popoff et al. |

FOREIGN PATENT DOCUMENTS

| | | |
|---|---|---|
| JP | 54-113445 | 9/1979 |
| JP | 61-068405 | 4/1986 |
| JP | 2002316971 A | 10/2002 |
| JP | 2007297391 A | 11/2007 |
| JP | 2007297392 A | 11/2007 |
| JP | 2008105951 A | 5/2008 |
| JP | 2011126885 A | 6/2011 |
| JP | 2013514352 A | 4/2013 |
| WO | 2009154086 A1 | 12/2009 |
| WO | 2010010756 A1 | 1/2010 |

OTHER PUBLICATIONS

Japanese Office Action for Application No. 2012-557244 dated May 7, 2014.

Extended European Search Report for Application No. 11754069.0 dated Jun. 10, 2015.

Extended European Search Report for Application No. 11754067.4 dated Jun. 10, 2015.

\* cited by examiner

STRUCTURED NON-AQUEOUS GEL-FORM CARRIER COMPOSITION

CROSS-REFERENCE TO RELATED APPLICATIONS

The present application is a national phase entry under 35 U.S.C. §371 of International Application No. PCT/US2011/027877 filed Mar. 10, 2011, published in English, which claims priority from U.S. Provisional Patent Application Nos. 61/312,552, and 61/312,429, both filed Mar. 10, 2010, all of which are incorporated herein by reference.

FIELD OF THE INVENTION

The present invention relates, in general, to non-aqueous gel-form carrier compositions for carrying active ingredients, and more particularly, to transparent or colored non-aqueous, structured, gel-form carrier compositions capable of carrying various types of active ingredients which, when used, elegantly deposit the actives onto a target substrate, possess good storage stability, particularly with respect to variations in temperature, and do not require the use of wax as a structuring agent (e.g., are wax-free).

BACKGROUND OF THE INVENTION

Conventional structured compositions typically employ various types of waxes as structuring agents in order to form user-friendly products having good stability properties, particularly with respect to temperature stability and good payoff. Payoff is a term used to describe both the amount of product applied onto a target substrate, as well as the way the product distributes onto the substrate. The problem with wax-based stick compositions is that they possess an undesirable waxy feel and inherently reduce the shine of any shine-imparting ingredients present in the stick composition.

Attempts have been made to formulate structured gel compositions in the absence of wax. For example, various types of polyamides have been commercialized as gellators/structuring agents in order to form solid compositions. Similarly, various glutamides, as well as various types of polyurethanes have also been employed in order to form solid, preferably clear, compositions. Such attempts, however, while successful at making solid compositions, possess numerous technical problems.

One of the technical problems involves the phenomenon known as "syneresis" whereby during storage of the solid compositions, particularly at slightly elevated temperatures, the surface of the solid composition develops distinct oil droplets which are not re-absorbed by the solid composition after its cooling to normal room temperature. Thus, the storage stability of such solid compositions leaves much to be desired.

Another technical problem relates to product pay-off. Some compositions having wax as structuring agents can have poor pay-off. Thus, in order to avoid such deposit issues, it is necessary that the product possess certain hardness/elasticity properties.

It is therefore an object of the present invention to provide non-aqueous, structured, gel-form carrier compositions capable of carrying various types of active ingredients that do not suffer from the aforementioned technical problems.

BRIEF SUMMARY OF TEE INVENTION

A first aspect of the present invention is directed to a non-aqueous composition that is capable of forming a gel structure, e.g., a soft gel or a hard or molded gel (such as a gel stick), comprising: a) a low molecular mass N-acyl glutamic acid diamide having a straight-chain alkyl group; b) a low molecular mass N-acyl glutamic acid diamide having a branched-chain alkyl group; c) at least one gel-promoting solvent; and either d) at least one high molecular mass block copolymer having at least one hard segment and at least one soft segment; and e) at least one solvent capable of solubilizing the at least one hard segment and/or the at least one soft segment of the block copolymer; or (d1) at least one oil-soluble polar modified polymer; and (e1) at least one solvent capable of solubilizing the at least one oil-soluble polar modified polymer; and optionally f) at least one active ingredient, wherein the composition has a hardness value ranging from about 30 to about 300 gramforce (gf), a melting point of about 50° C. or higher, does not require use of wax as a structuring agent (e.g., can be wax-free) and which may be transparent or colored in appearance.

Thus, in some embodiments, the non-aqueous carrier composition comprises: a) a low molecular mass N-acyl glutamic acid diamide having a straight-chain alkyl group; b) a low molecular mass N-acyl glutamic acid diamide having a branched-chain alkyl group; c) at least one gel-forming solvent; d) at least one high molecular mass block copolymer having at least one hard segment and at least one soft segment; e) at least one solvent capable of solubilizing the at least one hard segment and/or the at least one soft segment of the block copolymer; and optionally f) at least one active ingredient, wherein the composition has a hardness value ranging from about 30 to about 300 gramforce (gf), a melting point of about 50° C. or higher, does not require use of wax as a structuring agent (e.g., can be wax-free) and which may be transparent or colored in appearance.

In other embodiments, the non-aqueous carrier composition comprises: a) a low molecular mass N-acyl glutamic acid diamide having a straight-chain alkyl group; b) a low molecular mass N-acyl glutamic acid diamide having a branched-chain alkyl group; c) at least one gel-promoting solvent; (d1) at least one oil-soluble polar modified polymer; (e1) at least one solvent capable of solubilizing the at least one oil-soluble polar modified polymer; and optionally f) at least one active ingredient, wherein the composition has a hardness value ranging from about 30 to about 300 gramforce (gf), a melting point of about 50° C. or higher, does not require use of wax as a structuring agent (e.g., can be wax-free) and which may be transparent or colored in appearance.

Another aspect of the present invention is directed to a process for making the non-aqueous composition, comprising: a) providing a first composition, comprising: i) a low molecular mass N-acyl glutamic acid diamide having a straight-chain alkyl group; ii) a low molecular mass N-acyl glutamic acid diamide having a branched-chain alkyl group; iii) at least one gel-promoting solvent; b) providing a second composition, comprising: either i) at least one high molecular mass block copolymer having at least one hard segment and at least one soft segment; and ii) at least one solvent capable of solubilizing the at least one hard segment and/or the at least one soft segment of the block copolymer; or i-1) at least one oil-soluble polar modified polymer; and ii-1) at least one solvent capable of solubilizing the at least one oil-soluble polar modified polymer at a temperature of from about 90° C. to about 125° C.; and optionally iii) at least one active ingredient; c) mixing (a) and (b) at a temperature of from about 90° C. to about 125° C., to form a heated composition; and d) cooling the heated composition to form the non-aqueous, structured, gel-form composition, wherein the composition has a hardness value ranging from about 30 to about 300 gf, a melting point of about 50° C. or higher, does not require use of wax as a structuring agent (e.g., is wax-free) and may be transparent or colored in appearance.

Thus, in some embodiments, the process comprises: a) providing a first composition, comprising: i) a low molecular mass N-acyl glutamic acid diamide having a straight-chain alkyl group; ii) a low molecular mass N-acyl glutamic acid diamide having a branched-chain alkyl group; iii) at least one gel-promoting solvent; b) providing a second composition, comprising: i) at least one high molecular mass block copolymer having at least one hard segment and at least one soft segment; ii) at least one solvent capable of solubilizing the at least one hard segment and/or the at least one soft segment of the block copolymer; and optionally iii) at least one active ingredient; c) mixing (a) and (b) at a temperature of from about 90° C. to about 125° C., to form a heated composition; and d) cooling the heated composition to form the non-aqueous composition, wherein the composition has a hardness value ranging from about 30 to about 300 gf, a melting point of about 50° C. or higher, does not require use of wax as a structuring agent (e.g., is wax-free) and may be transparent or colored in appearance.

In other embodiments, the process for making the composition comprises: a) providing a first composition, comprising: i) a low molecular mass N-acyl glutamic acid diamide having a straight-chain alkyl group; ii) a low molecular mass N-acyl glutamic acid diamide having a branched-chain alkyl group; iii) at least one gel-promoting solvent; b) providing a second composition, comprising: i-1) at least one oil-soluble polar modified polymer; and ii-1) at least one solvent capable of solubilizing the at least one oil-soluble polar modified polymer at a temperature of from about 90° C. to about 125° C.; and optionally iii) at least one active ingredient; c) mixing (a) and (b) at a temperature of from about 90° C. to about 125° C., to form a heated composition; and d) cooling the heated composition to form the non-aqueous composition, wherein the composition has a hardness value ranging from about 30 to about 300 gf, a melting point of about 50° C. or higher, does not require use of wax as a structuring agent (e.g., is wax-free) and may be transparent or colored in appearance. Preparing the compositions at these temperatures minimizes both the cost, and degree of manufacturing difficulty.

DETAILED DESCRIPTION OF THE INVENTION

Figure 1:
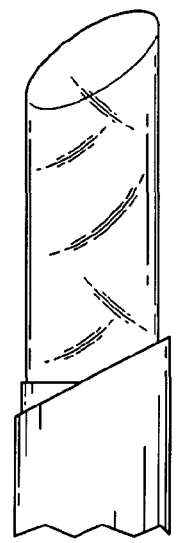
FIG. 1 is a color photograph of a composition according to one embodiment of the present invention.

Other than in the operating examples, or where otherwise indicated, all numbers expressing quantities of ingredients and/or reaction conditions are to be understood as being modified in all instances by the term "about" which as used herein refers to ±10-±15% of the referenced value.

As used herein, "structured" means gelled and/or rigidified.

"Transparent" is generally defined as having the property of transmitting rays of light through its substance so that bodies situated beyond or behind can be distinctly seen.

It has been surprisingly discovered that by combining certain low molecular mass organogellators with certain high molecular mass block copolymers, together with the appropriate solvents, non-aqueous, structured, gel carrier compositions capable of carrying various types of active ingredients can be made without the attendant disadvantages of significant syneresis and poor pay-off.

First Composition
Low Molecular Mass Organogellators

The composition of the present invention is formed by combining a first low molecular mass N-acyl glutamic acid diamide, or derivative thereof, having a straight-chain alkyl group, with a second low molecular mass N-acyl glutamic acid diamide, or derivative thereof, having a branched-chain alkyl group and at least one solvent capable of forming hydrogen bonds with the low molecular mass organogellators. The term "low molecular mass" as used herein refers to a molecular mass from greater than zero up to about 2,000 daltons.

It has also surprisingly been discovered by the inventor that the combination of at least one N-acyl glutamic acid diamide having a straight-chain alkyl group, such as dibutyl lauroyl glutamide, with at least one N-acyl glutamic acid diamide having a branched-chain alkyl group, such as dibutyl ethylhexanoyl glutamide, facilitates the formation of a gel carrier composition having optimal physical properties such as gel hardness sufficient to provide desired structure, low dissolution temperature, clarity and good payoff.

In a preferred embodiment, the dibutyl lauroyl glutamide is employed in an amount of from about 0.1 to about 50% by weight, such as from about 0.2 to about 40% by weight, and from about 0.3 to about 30% by weight, all weights being based on the total weight of the first composition. In a preferred embodiment, the dibutyl lauroyl glutamide is employed in an amount of from about 0.1 to about 10% by weight, such as from about 0.5 to about 5% by weight, and from about 1.0 to about 3.0% by weight, all weights being based on the total weight of the resultant composition.

Similarly, the dibutyl ethylhexanoyl glutamide is employed in an amount of from about 0.1 to about 50% by weight, such as from about 0.2 to about 40% by weight, and from about 0.3 to about 30% by weight, all weights being based on the total weight of the first composition. In a preferred embodiment, the dibutyl ethylhexanoyl glutamide is employed in an amount of from about 0.1 to about 10% by weight, such as from about 0.5 to about 5% by weight, and from about 1.0 to about 3% by weight, all weights being based on the total weight of the resultant composition.

In order to make a composition which is clear or transparent appearance (in which case they contain no pigment or less than about 0.5% pigment), the composition should employ the low molecular mass organogellators in a total amount of less than about 7% by weight, based on the weight of the composition.

The dibutyl lauroyl glutamide is commercially available as GP-1 and the dibutyl ethylhexanoyl glutamide is commercially available as EB-21, from Ajinomoto of Fort Lee, N J.

In a preferred embodiment, the straight alkyl-chain low molecular mass N-acyl glutamic acid diamide and branched alkyl-chain low molecular mass N-acyl glutamic acid diamide are employed in a ratio by weight of from about 1:1 to about 3:1, and preferably about 1.5:1.

Gel-Promoting Solvent

The low molecular mass organogellators of the present invention are solubilized in a solvent capable of gel-formation with the organogellators. Polar and non-polar solvents may be utilized, including, for example, alcohols, monoalcohols, dialcohols, acids, esters, and the like.

It is preferred to utilize a polar solvent. Preferred polar solvents include, but are not limited to, C2-C5 glycols, such as propylene glycol, butylene glycol and pentylene glycol. These solvents are believed to promote gel formation by inhibiting intercalation (intramolecular bonding) in the glutamide molecules. Other preferred solvents include, for example, octododecanol, isostearyl alcohol, and the like. Yet other preferred solvents include substituted hydrocarbyl siloxanes, as disclosed, for example, in U.S. Patent Application Publication 2004/0223936 A1. They are believed to promote hydrogen bond formation between molecules of the glutamides. One exemplary substituted hydrocarbyl siloxane is CARBINOL FLUID, bis-hydroxyethoxypropyl dimethicone, which is a hydrocarbyl functional organopolysiloxane having the formula, $R^1Me_2SiO(Me_2SiO)_xSiMe_2R^1$ where $R^1$ is —$(CH_2)_3OCH_2CH_2OH$, and x is such to provide the product with a viscosity of about 50 cS ($mm_2$/s) at 23° C. The solvents listed herein may be used individually or in combination of two or more.

It is preferred that the solvents be capable of dissolving said organogellators at a temperature of from about 90° C. to about 125° C.

The at least one gel-promoting solvent with the low molecular mass organogellators will typically be employed in an amount of from about 3 to about 50% by weight, such as from about 5 to about 40% by weight, and from about 7 to about 20% by weight, all weights being based on the total weight of the resultant composition. For purposes of making the compositions, the solvent is typically present in amounts ranging from about 10 to about 99% by weight, such as from about 20 to about 90% by weight, and from about 30 to about 80% by weight, all weights being based on the total weight of the first composition.

Second Composition
Block Copolymers

The second composition of the present invention is formed by combining at least one high molecular mass block copolymer having at least one hard segment and at least one soft segment with at least one solvent capable of solubilizing the hard and/or soft segment of the high molecular mass block copolymer.

The block copolymers of the present invention are characterized by the presence of at least one "hard" segment, and at least one "soft" segment. Aside from their compositional nature, the hard and soft segments of the block copolymers of the present invention are defined in terms of their respective glass transition temperatures, "$T_g$". More particularly, the hard segment has a $T_g$ of 50° C. or more, whereas the soft segment has a $T_g$ of 20° C. or less. The glass transition temperature $T_g$ for the hard block can range from 50° C. to 150° C.; 60° C. to 125° C.; 70° C. to 120° C.; 80° C. to 110° C. The glass transition temperature $T_g$ for the soft segment of the block copolymer can range from 20° C. to −150° C.; 0° C. to −135° C.; −10° C. to −125° C.; −25° C. to −100° C. A more in-depth explanation can be found in U.S. Pat. Nos. 5,294,438 and 6,403,070, the entire contents of which are hereby incorporated by reference.

One type of block copolymer which may be employed by the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention are block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics. It is preferred to utilize a mixture of diblock and triblock copolymers.

In some embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

The amounts of the block (co)polymer or (co)polymers, as well as their structure (di-block, tri-block, etc.), affect the nature of the thermoplastic elastomer, including its gelled form, which may range from fragile to soft/flexible to firm. For instance, soft gels contain relatively high amounts of soft segments, and firm gels contain relatively high amounts of hard segments. The overall properties of the composition may also be affected by including more than one such block copolymer e.g., including a mixture of copolymers. For example, the presence of tri-block copolymers enhances the integrity of the film formed. The gel may also be transparent, translucent or opaque, depending upon the other cosmetically acceptable ingredients added, as described herein.

It is preferred that the styrene content of the block copolymer be less than 30% by weight, preferably less than 25% by weight, and more preferably less than 20% by weight, based on the weight of the block copolymer. This is because of the tendency of block copolymers having a styrene content of greater than 30% by weight to harden/gel in conventional carrier systems. However, in the event that a block copolymer having a styrene content of greater than 30% by weight is used, it may be necessary to also employ a co-solvent or functional ingredient capable of dissolving a styrene block in an amount effective to control the hardening/gelling of the styrene-containing elastomer in the cosmetic composition.

A particularly preferred block copolymer for use in the present invention is a combination of di-block and tri-block copolymers of styrene-ethylene/butylene-styrene, commercially available from Shell Chemical Company under trade name Kraton G1657M. It should be noted, however, that any thermoplastic elastomer of the block copolymer type having at least one soft and at least one hard segment may be used without departing from the spirit of the invention.

The block copolymer is typically employed in an amount of from about 1 to about 40% by weight, such as from about 2 to about 20% by weight, and from about 3 to about 10% by weight, based on the total weight of the second composition. In a preferred embodiment, the block copolymer is employed in an amount of from about 1 to less than 10% by weight, such as from about 2 to about 8% by weight, and from about 3 to about 5% by weight, all weights being based on the total weight of the resultant composition.

In order to make a composition which is clear or transparent appearance, the composition should employ the high molecular mass block copolymer in an amount of less than about 10% by weight, based on the weight of the composition.

Other important considerations associated with the compositions of the present invention include syneresis/storage stability of the product, amount of active ingredient employed in the gel carrier composition, and hardness/elasticity/flexibility of the final product.

These properties are all affected by the weight ratio of low molecular mass organogellators to high molecular mass block copolymer present in the color cosmetic composition. If too much block copolymer is employed relative to the amount of low molecular mass organogellators, the resultant gel-form carrier composition exhibits: less transparency in appearance; increased hardness; decreased elasticity/flexibility; and poorer payoff.

The same effect is realized if too much low molecular mass organogellators are employed relative to the amount of block copolymer in the resultant gel-form carrier composition.

Thus, the ratio by weight of low molecular mass organogellators to high molecular mass block copolymer needs to be taken into account when making the gel carrier composition of the present invention, depending on its final intended use and desired appearance. Suitable ratios by weight of low molecular mass organogellators to high molecular mass block copolymers include from about 1:1 to about 2:1, such as from about 3:1 to about 4:1, and from about 5:1 to about 6:1.

Similarly, the ratio by weight of high molecular mass block copolymer to low molecular mass organogellators needs to be taken into account when making the gel carrier composition of the present invention, depending on its final intended use and desired appearance. Suitable ratios by weight of high molecular mass block copolymers to low molecular mass organogellators include from about 1:1 to about 2:1, such as from about 3:1 to about 4:1, and from about 5:1 to about 6:1.

Solvent for Block Copolymer

Solvents capable of solubilizing the hard and/or soft segment of the block copolymer which may be used herein are typically characterized in terms of their ability to solubilize the block copolymer at a temperature of from about 90 to about 125° C.

Nonvolatile solvents capable of solubilizing the hard segment of the block copolymer which can be used in the invention include, but are not limited to, monoesters, diesters, triesters, mixed aliphatic and/or aromatic, polar oils such as: hydrocarbon-based oils of animal origin, such as perhydrosqualene; hydrocarbon-based plant oils such as liquid triglycerides of fatty acids and of glycerol, in which the fatty acids may have varied chain lengths, these chains being linear or branched, and saturated or unsaturated; these oils can be chosen, for example, from wheat germ oil, sunflower oil, corn oil, soybean oil, marrow oil, grapeseed oil, blackcurrant seed oil, sesame oil, hazelnut oil, apricot oil, macadamia oil, castor oil, avocado oil, karite butter, sweet almond oil, cotton oil, alfalfa oil, poppy oil, pumpkin oil, evening primrose oil, millet oil, barley oil, quinoa oil, olive oil, rye oil, safflower oil, candlenut oil, passion flower oil, musk rose oil and caprylic/capric acid triglycerides such as those sold by the company Stéarineries Dubois or those sold under the names Miglyol 810, 812 and 818 by the company Dynamit Nobel; natural or synthetic esters of formula $R_1COOR_2$, wherein $R_1$ is a higher fatty acid residue comprising 7 to 19 carbon atoms, and $R_2$ is a branched hydrocarbon-based chain comprising 3 to 20 carbon atoms, such as, for example, purcellin oil (cetostearyl octanoate), isopropyl myristate and alkyl or polyalkyl octanoates, decanoates or ricinoleates; synthetic ethers of formula $R^3COR^4$, wherein $R^3$ is a $C_3$ to $C_{19}$ alkyl radical, and $R^4$ is a $C_3$ to $C_{20}$ alkyl radical; fatty alcohols comprising at least 12 carbon atoms, such as octyldodecanol or oleyl alcohol; cyclic hydrocarbons such as (alkyl)cycloalkanes, wherein the alkyl chain is linear or branched, saturated or unsaturated and comprises 1 to 30 carbon atoms, such as cyclohexane or dioctylcyclohexane; aromatic hydrocarbons, for example, alkenes such as benzene, toluene, 2,4-dimethyl-3-cyclohexene, dipentene, p-cymene, naphthalene or anthracene, and esters such as isostearyl benzoate; primary, secondary or tertiary amines such as triethanolamine; and mixtures thereof. In one embodiment, synthetic esters such as isopropyl myristate are used.

Preferred esters are those having a weight average molecular weight (Mw) in the range of 100 to 600, preferably from 100 to 500. Examples thereof include, but are not limited to, C12-15 alkyl benzoate, isopropyl myristate (Mw=270), isopropyl palmitate (Mw=300), isononyl isononanoate, cetyl ethylhexanoate (Mw=368), neopentyl glycol diethylhexanoate (Mw=356), diisopropyl sebacate (Mw=286).

The solvent capable of solubilizing the soft segment of the block copolymer may be selected from volatile solvents and nonvolatile solvents. The expression "volatile solvent" means a solvent that is capable of evaporating at room temperature from a support onto which it has been applied, in other words a solvent which has a measurable vapor pressure at room temperature. See, U.S. Pat. No. 6,656,458, the entire content of which is hereby incorporated by reference.

Representative examples of suitable volatile organic solvents include, but are not limited to, volatile hydrocarbon-based oils. The expression "hydrocarbon-based oil" means oil containing only hydrogen and carbon atoms. Examples of volatile hydrocarbon-based oils include isoparaffins, i.e., branched alkanes containing from 8 to 16 carbon atoms, and in particular isododecane (also known as 2,2,4,4,6-pentamethylheptane). It is also possible to use mixtures of such isoparaffins. Other volatile hydrocarbon-based oils, such as petroleum distillates, can also be used.

Suitable nonvolatile solvents which can be used are those having a weight average molecular weight in the range of 150 to 450, preferably from 200 to 350. Examples thereof include, but are not limited to, hydrogenated polydecene, hydrogenated polyisobutene, isoeicosane, polydecene and polybutene.

The solvent capable of solubilizing the high molecular mass block copolymer, at a temperature of from about 90 to about 125° C., is typically present in an amount of from about 10% to about 99% by weight, such as from about 20 to about 90% by weight, and from about 30 to about 80% by weight, based on the total weight of the second composition. In a preferred embodiment, the solvent capable of solubilizing the high molecular mass block copolymer is employed in an amount of from about 10 to about 50% by weight, such as from about 15 to about 40% by weight, and from about 20 to about 30% by weight, all weights being based on the total weight of the resultant composition.

In some embodiments, the compositions contain an oil-soluble polar modified polymer and a solvent.

Polar Modified Polymer

"Polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, C2-C20 compounds such as, for example, styrene, ethylene, propylene, isopropylene, butylene, isobutylene, pentene, isopentene, isoprene, hexene, isohexene, decene, isodecene, and octadecene, including all ranges and subranges therebetween. Preferably, the monomers are C2-C8 compounds, more preferably C2-C6 compounds, and most preferably C2-C4 compounds such as ethylene, propylene and butylene.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to the present invention, the polar modified polymer is oil-soluble: that is, the polymer does not contain a sufficient amount of hydrophilic unit(s) to render the entire polymer water-soluble or oil-insoluble. According to preferred embodiments, the polar modified polymer contains the same amount of hydrophobic monomer as hydrophilic unit (1:1 ratio) or more hydrophobic monomer than hydrophilic unit. According to particularly preferred embodiments, the polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the polar modified polymer is a wax. According to particularly preferred embodiments, the polar modified wax is made via metallocene catalysis, and includes polar groups or units as well as a hydrophobic backbone. Suitable modified waxes include those disclosed in U.S. Patent Application Publication No. 2007/0031361, the entire contents of which is hereby incorporated by reference. Particularly preferred polar modified waxes are C2-C3 polar modified waxes.

In accordance with preferred embodiments of the present invention, the polar modified wax is based upon a homopolymer and/or copolymer wax of hydrophobic monomers and has a weight-average molecular weight Mw of less than or equal to 25,000 g/mol, preferably of 1000 to 22,000 g/mol and particularly preferably of 4000 to 20,000 g/mol, a number-average molecular weight Mn of less than or equal to 15,000 g/mol, preferably of 500 to 12,000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Polar modified waxes can be produced in a known manner from the homopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the C2-C3 wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred $C_2$-$C_3$ polar modified waxes for use in the present invention are polypropylene and/or polyethylene-maleic anhydride modified waxes ("PEMA," "PPMA." "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; Drop Point, Mettler: 106° C.) from Honeywell, A-C 596 A (PROPYLENE-MALEIC ANHYDRIDE COPOLYMER; Drop Point, Mettler: 143° C.) from Honeywell, A-C 597 (PROPYLENE-MALEIC ANHYDRIDE COPOLYMER; Drop Point, Mettler: 141° C.) from Honeywell, ZeMac® copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemical Co., poly(ethylene-co-butyl acrylate-co-maleic anhydride) sold under the trade name of Lotader (e.g., 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the Lotader name, and isobutylene maleic anhydride copolymer sold under the name ACO-5013 by ISP.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orientation (for example, atactic, isotactic or syndiotactic along the backbone).

The polar modified polymer(s) is typically represent from about 1% to about 20% by weight, preferably from about 2% to about 15% by weight, and more preferably from about 3% to about 10% by weight, including all ranges and subranges therebetween, the weight being based on the total weight of the composition. For purposes of making the compositions, the polar modified polymer is typically present in amounts ranging from about 10-40%, preferably 12-30% and more preferably 14-20%, by weight of the second composition.

Solvent for Oil-Soluble Polar Modified Polymer

Solvents capable of solubilizing the oil-soluble polar modified polymer include, for example, volatile and/or non-volatile oils. Such oils can be any acceptable oil including but not limited to silicone oils and/or hydrocarbon oils.

According to preferred embodiments, the solvent comprises one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other preferred embodiments, the solvent comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched C8 to C16 alkanes such as C8 to C16 isoalkanes (also known as isoparaffins), isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

Further examples of non-volatile oils that may be used in the present invention include, but are not limited to, polar oils such as:

a. hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

b. synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

c. synthetic ethers containing from 10 to 40 carbon atoms;

d. $C_8$ to $C_{26}$ fatty alcohols, for instance oleyl alcohol; and e. mixtures thereof.

Examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

The solvent for the oil-soluble polar modified polymer may be employed in an amount of from about 5 to about 50% by weight, preferably from about 10 to about 40% by weight, and more preferably from about 15 to about 30% by weight, and all subranges therebetween, all weights being based on the total weight of the composition. For purposes of making the composition, the solvent for the oil-soluble polar modified polymer may be employed in an amount of from about 50 to about 90% by weight, preferably from about 55 to about 80% by weight, and more preferably from about 60 to about 70% by weight, based on the total weight of the second composition.

Active Ingredients (Optional)

The purpose of the transparent non-aqueous, structured gel carrier composition of the present invention is to carry active ingredients for application onto a variety of target substrates. Various types of active ingredients may be carried by the gel carrier composition. Examples of suitable active ingredients include, for example, colorants such as pigments, inks and lakes; dermatological ingredients such as sunscreen agents, anti-acne agents, anti-aging compounds; insect repelling agents; transdermal pharmaceutical compounds; deodorant and antiperspirant agents; perfumes; dye compounds; etc.

The type and amount of active ingredient to be employed will depend on the ultimate use of the composition, and is to be determined by those of ordinary skill in the art. For example, the compositions may be used as lip gloss, mascara, hair styling compositions and the like. Typically, to make a composition that is non-transparent and thus colored in appearance, the amount of colorant will be greater than about 0.5% by weight of the composition. Inventive compositions that are transparent contain colorant but in an amount less than about 0.5% by weight. The active ingredient (e.g., colorant) is present in amounts generally ranging from about 0.01 to 20 wt % and in some embodiments from about 0.1 to about 10% by weight, based on the total weight of the composition.

The non-aqueous, structured, compositions should be stable under conventional storage conditions. In order to achieve storage stability, the composition must have a melting point of about 50° C. or higher, such as 90° C. or higher, and 110° C. or higher.

Figure 2:
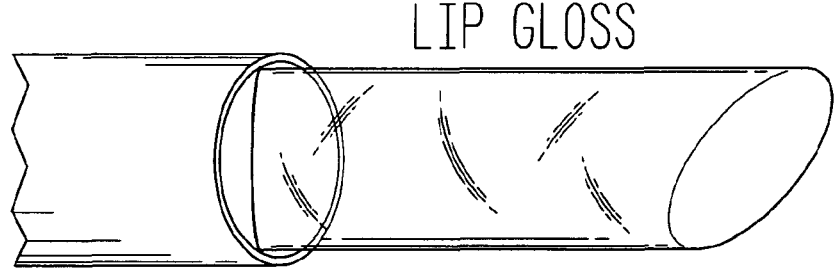
FIG. 2 is a color photograph of the composition of FIG. 1.
Figure 3:
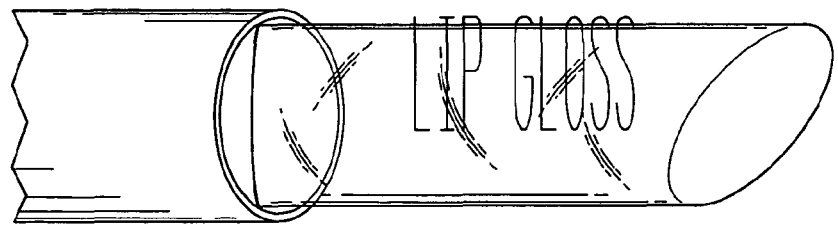
FIG. 3 is a color photograph of the composition of FIG. 1.

FIG. 1 is a color photograph of a composition according to one embodiment of the present invention. As is evident from the photograph, the composition is transparent in appearance. FIG. 2 is a color photograph of the composition of FIG. 1. The image shows the composition adjacent an image of a lipstick. In addition to being transparent, the composition has a magnification effect whereby the image appears larger when viewed through the composition. FIG. 3 is a color photograph of the composition of FIG. 1. This is another example of the magnification effect of the composition.

The compositions should also have good "pay-off", i.e., the ability to be elegantly and uniformly deposited onto a targeted substrate. This property is dependent on the hardness of the composition. The hardness of the composition may, for example, be expressed in gramforce (gf). The composition of the present invention may, for example, have a hardness ranging from about 30 gf to about 300 gf, such as from about 50 gf to about 120 gf, and further such as from about 60 gf to about 100 gf.

Hardness is measured in one of two ways. A first test for hardness entails penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is known as the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value obtained from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on a targeted substrate. In addition, this hardness may impart good impact strength to the inventive compositions, which may be molded, cast, or extruded, for example, in stick or dish form.

According to anther aspect of the present invention, there is provided a process for making a non-aqueous, structured color cosmetic composition. The process involves forming the above-described first and second compositions by combining their respective ingredients at a temperature of from about 90 to about 125° C., followed by combining the first and second compositions at a temperature of from about 90 to about 125° C. Preparing the compositions at these temperatures minimizes both the cost, and degree of manufacturing difficulty.

The present invention will be better understood from the examples which follow, all of which are intended for illustrative purposes only, and are not meant to unduly limit the scope of the invention in any way.

EXAMPLES

High Molecular Mass Gelator Liquid Phase

| Name | EX1 |
| --- | --- |
| HYDROGENATED STYRENE/BUTADIENE COPOLYMER | 11.1 |
| HYDROGENATED STYRENE/METHYL STYRENE/INDENE COPOLYMER | 33.3 |
| HYDROGENATED POLYDECENE (QS) | 55.6 |
| Total Phase A | 100 |

Procedure:

Heated the hydrogenated polydecene to 100° C. Added the hydrogenated styrene/butadiene copolymer to the oil phase and mixed the two until the polymer solution became clear and homogeneous. Added the hydrogenated styrene/methyl styrene/indene copolymer to the polymer solution and mixed until the mixture is dissolved and clear. Allowed the mixture to cool down to room temperature.

Low Molecular Mass Gelator Gel Phase

| Name | EX2 | EX3 | EX4 |
| --- | --- | --- | --- |
| ISOSTEARYL ALCOHOL | 66.7 | | |
| OCTYLDODECANOL | | 75 | |
| BUTYLENE GLYCOL | | | 55.56 |
| DIBUTYL ETHYL GLUTAMIDE | 13.3 | 10 | 22.22 |
| DIBUTYL LAUROYL GLUTAMIDE | 20 | 15 | 22.22 |
| Total Phase B | 100 | 100 | 100 |

Procedure:

the organogelators with the alcohol. Heated the solution to: about 115° C. in Ex. 2; about 116° C. in Ex 3; and about 102° C. in Ex. 4; until the organogelators were dissolved. Cooled the resultant organogelator solution to room temperature.

Examples 5 & 6

Crystal Clear Lipstick Formulations

| Name | EX5 | EX6 |
| --- | --- | --- |
| Polymer solution (From Ex1) | 27 | 27 |
| Gel (From Ex3) | 20 | 9 |
| ISOEICOSANE | 12 | 12 |
| NEOPENTYL GLYCOL DICAPRATE | 10 | 10 |
| SUCROSE ACETATE ISOBUTYRATE | 10 | 10 |
| BEHNYL/ISOSTEARYL/PHYTOSTEARYL DIMER DILINOLEYL DIMER DILINOLEATE | 5 | 5 |
| STEARYL HEPTANOATE | 5 | 5 |
| TRICAPRYLIN (QS) | 11 | 12 |
| TRIMETHYL PENTAPHENYL TRISILOXANE | 0 | 10 |
| Total | 100 | 100 |

Procedure:

Heated the oils with stirring to 125° C. Added the gel prepared in Ex 3. Mixed until homogenous. Added the polymer solution prepared in Ex 1. Mixed until homogenous and a clear solution was formed. Poured the hot solution into a mold. Once the solution set in the mold, placed the mold in the freezer for about 30 minutes. The resultant product was a clear lipstick in hard gel form.

| Name | EX7 |
| --- | --- |
| Material (From Ex1) | 27 |
| Gel (From Ex2) | 9 |
| ISOEICOSANE | 15 |
| HYDROGENATED POLYDECENE | 15 |
| SUCROSE ACETATE ISOBUTYRATE | 10 |
| TRICAPRYLIN | 14 |
| PHENYL TRIMETHICONE | 10 |
| Total | 100 |

Procedure:

Heated the material from Ex 1 with ISOEICOSANE, HYDROGENATED POLYDECENE and PHENYL TRIMETHICONE to 120° C. with mixing. Separately heated the Gel of Ex 2 with SUCROSE ACETATE ISOBUTYRATE and TRICAPRYLIN to 120° C. with mixing. Once both phases were homogenous, combined and mixed them. Poured the hot solution into the mold. Once the solution set in the mold, placed the mold in the freezer for about 30 minutes. The resultant product was a clear lipstick in hard gel form.

Example 8

Transparent Stick

| Name | EX8 |
| --- | --- |
| HYDROGENATED STYRENE/BUTADIENE COPOLYMER | 3 |
| HYDROGENATED STYRENE/METHYL STYRENE/INDENE COPOLYMER | 9 |
| HYDROGENATED POLYDECENE | 25 |
| ISOSTEARYL ALCOHOL | 6 |
| DIBUTYL ETHYL GLUTAMIDE | 1.2 |
| DIBUTYL LAUROYL GLUTAMIDE | 1.8 |
| ISOEICOSANE | 20 |
| SUCROSE ACETATE ISOBUTYRATE | 10 |
| TRICAPRYLIN | 7 |
| BEHNYL/ISOSTEARYL/PHYTOSTEARYL DIMER DILINOLEYL DIMER DILINOLEATE | 5 |
| STEARYL HEPTANOATE | 2 |
| TRIMETHYL PENTAPHENYL TRISILOXANE | 10 |
| TOTAL | 100 |

Procedure:

Heated HYDROGENATED POLYDECENE with HYDROGENATED STYRENE/BUTADIENE COPOLYMER TO 110° C. while mixing. Added HYDROGENATED STYRENE/METHYL STYRENE/INDENE COPOLYMER while mixing until homogenous, [Gel of Phase A (Ex 1)]. Added ISOEICOSANE, remaining HYDROGENATED POLYDECENE and TRIMETHYL PENTAPHENYL TRISILOXANE while mixing. Separately, heated ISOSTEARYL ALCOHOL, DIBUTYL ETHYL GLUTAMIDE and DIBUTYL LAUROYL GLUTAMIDE [Gel of Phase B (Ex 2)] with SUCROSE ACETATE ISOBUTYRATE, -BEHNYL/ISOSTEARYL/PHYTOSTEARYL DIMER DILINOLEYL DIMER DILINOLEATE, STEARYL HEPTANOATE and TRICAPRYLIN to 110° C. while mixing. Once both phases were homogenous, combined and mixed. Poured the hot solution into the mold. Once the solution set in the mold, put the mold in the freezer for about 30 minutes. The resultant product was a clear lipstick in hard gel form.

Example 9

Transparent Color Stick

| Name | EX9 |
|---|---|
| HYDROGENATED STYRENE/BUTADIENE COPOLYMER | 3.5 |
| HYDROGENATED STYRENE/METHYL STYRENE/INDENE COPOLYMER | 10.5 |
| HYDROGENATED POLYDECENE | 27.5 |
| ISOSTEARYL ALCOHOL | 7 |
| DIBUTYL ETHYL GLUTAMIDE | 1.4 |
| DIBUTYL LAUROYL GLUTAMIDE | 2.1 |
| ISOEICOSANE | 15 |
| SUCROSE ACETATE ISOBUTYRATE | 10 |
| TRICAPRYLIN | 8 |
| BEHNYL/ISOSTEARYL/PHYTOSTEARYL DIMER DILINOLEYL DIMER DILINOLEATE | 5 |
| PHENYL TRIMETHICONE | 10 |
| COLORANT | 0.05 |
| TOTAL | 100 |

Procedure:

Heated HYDROGENATED POLYDECENE with HYDROGENATED STYRENE/BUTADIENE COPOLYMER TO 120° C. while mixing. Added HYDROGENATED STYRENE/METHYL STYRENE/INDENE COPOLYMER while mixing until homogenous, [Gel of Phase A (Ex 1)]. Added ISOEICOSANE, remaining HYDROGENATED POLYDECENE and PHENYL TRIMETHICONE while mixing. Separately, heated ISOSTEARYL ALCOHOL, DIBUTYL ETHYL GLUTAMIDE and DIBUTYL LAUROYL GLUTAMIDE [Gel of Phase B (Ex 2)] with SUCROSE ACETATE ISOBUTYRATE, -BEHNYL/ISOSTEARYL/PHYTOSTEARYL DIMER DILINOLEYL DIMER DILINOLEATE and TRICAPRYLIN to 120° C. while mixing. Once both phases were homogenous, combined and mixed. Added COLORANT and mixed until homogenous. Poured the hot solution into the mold. Once the solution set in the mold, put the mold in the freezer for about 30 minutes. The resultant product was a clear lipstick in hard gel form.

Example 10

Clear Stick with Active Ingredients

| Name | EX10 |
|---|---|
| HYDROGENATED STYRENE/BUTADIENE COPOLYMER | 3.5 |
| HYDROGENATED STYRENE/METHYL STYRENE/INDENE COPOLYMER | 10.5 |
| HYDROGENATED POLYDECENE | 26.5 |
| ISOSTEARYL ALCOHOL | 7 |
| DIBUTYL ETHYL GLUTAMIDE | 1.4 |
| DIBUTYL LAUROYL GLUTAMIDE | 2.1 |
| ISOEICOSANE | 15 |
| SUCROSE ACETATE ISOBUTYRATE | 10 |
| TRICAPRYLIN | 8 |
| BEHNYL/ISOSTEARYL/PHYTOSTEARYL DIMER DILINOLEYL DIMER DILINOLEATE | 5 |
| PHENYL TRIMETHICONE | 10 |
| ACTILIPID* | 1 |
| TOTAL | 100 |

*Denotes a combination of *TRITICUM VULGARE* GERM EXTRACT, *OLEA EUROPAEA* FRUIT EXTRACT, *COLEUS FORSKOHLII* ROOT EXTRACT, *POLYGONUM CUSPIDATUM* EXTRACT and *HELIANTHUS ANNUUS* SEED OIL Procedure:

Heated HYDROGENATED POLYDECENE with HYDROGENATED STYRENE/BUTADIENE COPOLYMER TO 120° C. while mixing. Added HYDROGENATED STYRENE/METHYL STYRENE/INDENE COPOLYMER while mixing until homogenous, [Gel of Phase A (Ex 1)]. Added ISOEICOSANE, remaining HYDROGENATED POLYDECENE and PHENYL TRIMETHICONE while mixing. Separately, heated ISOSTEARYL ALCOHOL, DIBUTYL ETHYL GLUTAMIDE and DIBUTYL LAUROYL GLUTAMIDE [Gel of Phase B (Ex 2)] with SUCROSE ACETATE ISOBUTYRATE, -BEHNYL/ISOSTEARYL/PHYTOSTEARYL DIMER DILINOLEYL DIMER DILINOLEATE and TRICAPRYLIN to 120° C. while mixing. Once both phases were homogenous, combined and mixed. Added ACTILIPID and mixed until homogenous. Poured the hot solution into the mold. Once the solution set in the mold, put the mold in the freezer for about 30 minutes. The resultant product was a clear lipstick in hard gel form.

Example 11

Gel Stick

| Name | EX8 |
|---|---|
| OCTYLDODECANOL | 12.54 |
| DIBUTYL ETHYL GLUTAMIDE | 1 |
| DIBUTYL LAUROYL GLUTAMIDE | 2 |
| ISOHEXADECANE | 4.3 |
| Poly propylene-ethylene-maleic anhydride copolymer | 10 |
| cyclopentasiloxane | 50.16 |
| OCTYLDODECYL NEOPENTANOATE | 20 |
| TOTAL | 100 |

Procedure:

Heated OCTYLDODECANOL, DIBUTYL ETHYL GLUTAMIDE and DIBUTYL LAUROYL GLUTAMIDE at 125° C. until gellants were fully dispersed. Separately, heated Octyldodecyl neopentanoate, isohexadecane, cyclopentasiloxane with poly propylene-ethylene-maleic anhydride copolymer to 100° C. during mixing until the polymer solution became homogeneous. Once both phases were homogenous, combined and mixed. Reduced the solution temperature to 50° C. and poured the hot solution into the mold. Once the solution set in the mold, put the mold in the freezer for about 30 minutes. The resultant product was a gel stick.

Example 12

| Name | EX8 |
|---|---|
| Propylene glycol | 10.0 |
| DIBUTYL ETHYL GLUTAMIDE | 1.0 |
| DIBUTYL LAUROYL GLUTAMIDE | 1.5 |
| ISOHEXADECANE | 4.3 |
| Poly propylene-ethylene-maleic anhydride copolymer | 10 |
| Carbinol fluid | 29.28 |
| OCTYLDODECYL NEOPENTANOATE | 43.92 |
| TOTAL | 100 |

Heated propylene glycol, DIBUTYL ETHYL GLUTAMIDE and DIBUTYL LAUROYL GLUTAMIDE at 100° C.

until gellants fully dispersed. Separately, heated Octyldodecyl neopentanoate, isohexadecane, carbinol fluid with poly propylene-ethylene-maleic anhydride copolymer to 100° C. during mixing until the polymer solution became homogeneous. Once both phases were homogenous, combined and mixed. Reduced the solution temperature to 70° C. and poured the hot solution into the mold. Once the solution set in the mold, put the mold in the freezer for about 30 minutes. The resultant product was a gel stick.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A non-aqueous carrier composition capable of forming a gel structure comprising:
   a) a structuring agent consisting of a') N-acyl glutamic acid diamide having a straight-chain alkyl group comprising dibutyl lauroyl glutamide, and an
   a") N-acyl glutamic acid diamide having a branched-chain alkyl group comprising dibutyl ethylhexanoyl glutamide;
   b) at least one gel-promoting solvent, wherein said gel-promoting solvent is capable of dissolving said dibutyl ethylhexanoyl glutamide and said dibutyl lauroyl glutamide at a temperature of from about 90° C. to about 125° C.;
   c) at least one block copolymer having at least one hard segment and at least one soft segment; and
   d) at least one solvent capable of solubilizing the at least one hard segment and/or the at least one soft segment of the block copolymer; and optionally
   e) at least one active ingredient, wherein the composition has a hardness value ranging from about 30 to about 300 gf, and a melting point of about 50° C. or higher, and wherein the composition is free of antiperspirant agent.

2. The composition of claim 1 wherein (a') is present in an amount of from about 0.1 to about 10% by weight, based on the total weight of the composition.

3. The composition of claim 1 wherein (a") is present in an amount of from about 0.1 to about 10% by weight, based on the total weight of the composition.

4. The composition of claim 1 wherein (b) is chosen from a C2-C5 glycol, an isostearyl alcohol and mixtures thereof.

5. The composition of claim 1 wherein (b) is present in an amount of from about 3 to about 50% by weight, based on the total weight of the composition.

6. The composition of claim 1 wherein (c) is a mixture of diblock and triblock copolymers.

7. The composition of claim 1 wherein (c) is present in an amount of from about 1 to about 10% by weight, based on the total weight of the composition.

8. The composition of claim 1 wherein (d) is hydrogenated polydecene.

9. The composition of claim 1 wherein (d) is present in an amount of from about 10 to about 50% by weight, based on the total weight of the resultant composition.

10. The composition of claim 1 wherein (a') and (a") are present in a total amount of less than 7% by weight, (c) is present in an amount of less than 10% by weight, all weights being based on the weight of the composition, and the composition is transparent in appearance.

11. The composition of claim 1, further comprising an active ingredient.

12. The composition of claim 11, wherein the active ingredient is a colorant.

13. A process for making a non-aqueous carrier composition capable of forming a gel structure, comprising:
   a) mixing a first composition and second composition at a temperature of about 90° C. to about 125° C., to form a heated composition,
   wherein the first composition comprises:
   i) a structuring agent consisting of a N-acyl glutamic acid diamide having a straight-chain alkyl group comprising dibutyl lauroyl glutamide and
   ii) a N-acyl glutamic acid diamide having a branched-chain alkyl group comprising dibutyl ethylhexanoyl glutamide; and
   iii) at least one gel-promoting solvent, wherein said gel-promoting solvent is capable of dissolving said dibutyl ethylhexanoyl glutamide and said dibutyl lauroyl glutamide at a temperature of from about 90° C. to about 125° C.; and
   wherein the second composition comprises:
   i) at least one block copolymer having at least one hard segment and at least one soft segment; and
   ii) at least one solvent capable of solubilizing the at least one hard segment and/or the at least one soft segment of the block copolymer;
   and optionally at least one active ingredient; and
   b) cooling the heated composition to form the non-aqueous, structured, gel-form composition, wherein the composition has a hardness value ranging from about 30 to about 300 gf, and a melting point of about 50° C. or higher, wherein the composition is free of antiperspirant agent.

14. The process of claim 13, wherein the second composition further comprises at least one oil-soluble polar modified polymer; and
   at least one solvent capable of solubilizing the at least one oil-soluble polar modified polymer.

15. The process of claim 13, wherein the second composition further comprises the active ingredient.

* * * * *